United States Patent
Argabrite

[11] 3,965,727
[45] June 29, 1976

[54] HARDNESS TESTING INSTRUMENT

[76] Inventor: George A. Argabrite, c/o Pacific Transducer Corporation, 2301 Federal Ave., Los Angeles, Calif. 90064

[22] Filed: Oct. 17, 1974

[21] Appl. No.: 515,654

[52] U.S. Cl. ............................................. 73/81
[51] Int. Cl.² ........................................ G01N 3/48
[58] Field of Search ............................. 73/81, 85

[56] References Cited
UNITED STATES PATENTS

| | | | |
|---|---|---|---|
| 1,802,685 | 4/1931 | Trier | 73/81 |
| 1,875,862 | 9/1932 | Fair | 73/81 |
| 2,436,435 | 2/1948 | Kent | 73/85 |
| 2,656,716 | 10/1953 | Hoggatt | 73/81 |
| 2,976,732 | 3/1961 | Hautly | 116/114 AH |

Primary Examiner—James J. Gill
Assistant Examiner—Anthony V. Ciarlante
Attorney, Agent, or Firm—Poms, Smith, Lande & Glenny

[57] ABSTRACT

An instrument for measuring and indicating the hardness of such compressible materials as plastic foam compositions, including a frame adapted to be conveniently manipulated by the user, an indentor movably mounted in the frame and resiliently biased downwardly relative to the frame, the indentor having a downwardly directed thin elongated convex marking edge projecting through an elongated slot formed in a lower plate of the frame. The plate has a lower contour matingly congruent with the contour of the sample to be tested, and its relatively large area serves to limit downward movement of the frame toward the sample; thus, the length of the line of penetration of the indentor marking edge into the sample becomes a measure of the density of the sample. Desirably the marking edge is preliminarily colored by a suitable material, such as being rolled on a conventional stamp inking pad; after testing, the length of the colored line on the sample, suitably calibrated, is a measure of the hardness of the sample and, indirectly, of its density. A longitudinal scale is provided on the frame for convenience in measuring the length of the indented line. The instrument includes calibration means, comprising a horizontally disposed calibration bar which may be selectively adjustable in position relative to the frame, and which serves as the upper abutment for resilient means in the form of compression springs bearing downwardly on the indentor. Limit means are provided on the indentor for establishing the lower rest or inoperative position of the indentor, including a pair of spaced legs fixed to the blade near opposite ends thereof and extending upwardly through frame openings, the legs having upper enlargements abuttable downwardly against the frame adjacent to the openings.

6 Claims, 5 Drawing Figures

U.S. Patent June 29, 1976 3,965,727
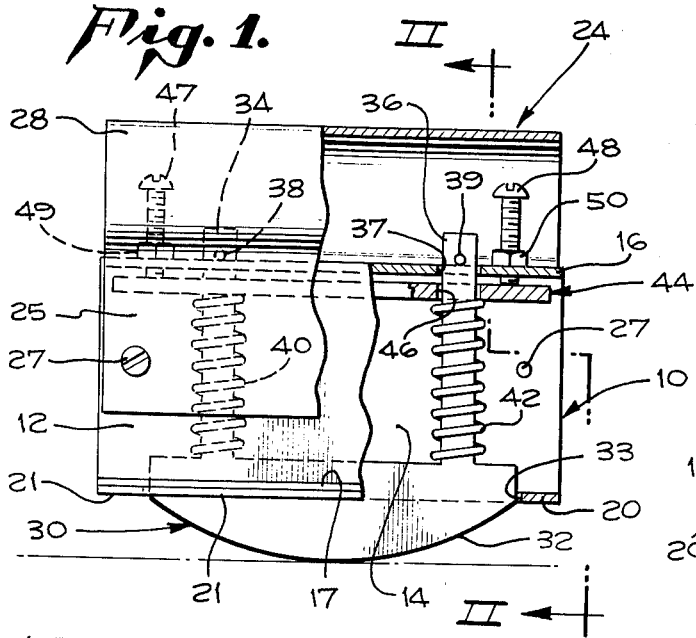
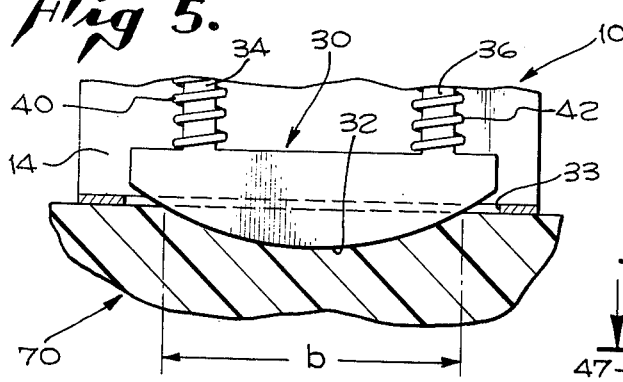
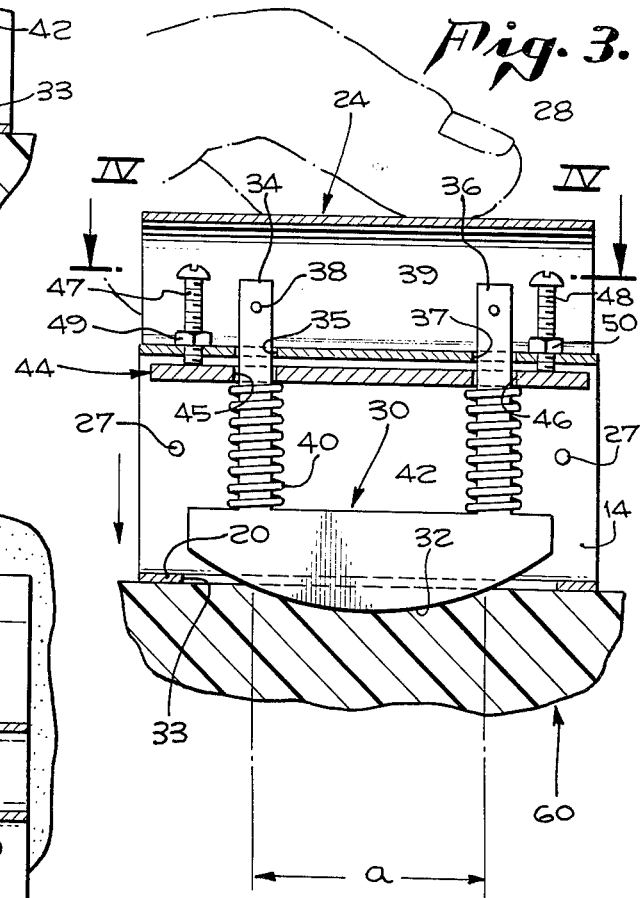
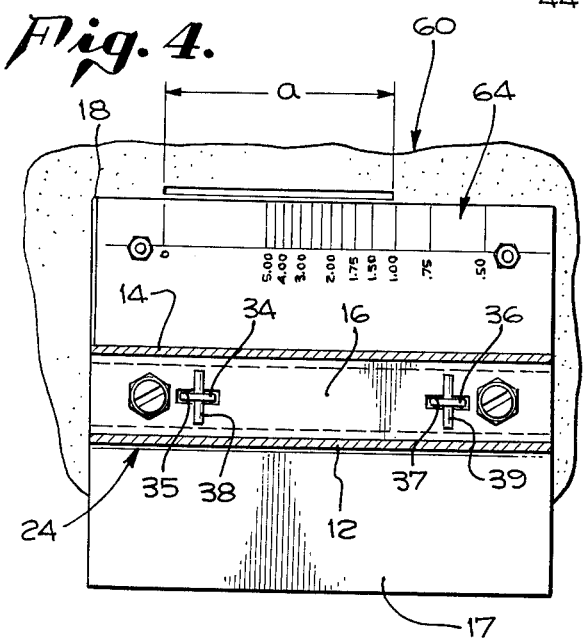

HARDNESS TESTING INSTRUMENT

BACKGROUND AND SUMMARY OF THE INVENTION

The present invention relates generally to hardness testing of a sample, and is more particularly directed to an instrument for measuring and indicating the hardness of a sample of plastic foam, both of the relatively rigid type such as polystyrene as well as more resilient plastic foam material. It may be noted that, for any given plastic foam material, the density of the material is a function of its hardness, and as a consequence, the present instrument may be calibrated to yield a reading of density.

In the preferred form of the invention hereinafter described and illustrated, there is provided a frame which may be easily grasped by the user, the frame having mounted thereon a thin elongated rigid indentor, preferably of rigid metal, provided with a downwardly convex marking edge. The exact contour of the marking edge may be selected to be particularly adapted for a specific material of a sample to be measured; in the present embodiment of the invention, the contour of the marking edge is that of a portion of a circle which may have a radius, for example, of 2 or 3 inches. The frame includes a lower plate having a contour which is matingly congruent to the contour of a sample to be tested, and is provided with a thin elongated slot for loosely receiving the indentor therein. In the present illustrative form of the invention, the contour of the lower plate is planar for simplicity of description and illustration, but it will be understood that the plate contour could be of other shapes, to be matingly congruent with a sample. The plate serves as a means for limiting movement of the frame in the direction of the sample so that the frame proper will not penetrate the sample.

Calibration means are provided for selectively adjusting the amount of compression exerted by the resilient means biasing the indentor downwardly relative to the frame. Such means in the preferred form of the invention include a calibration bar against which the resilient biasing means abut for urging the marking edge into the sample, and means for selectively adjusting the position of the calibration bar relative to the frame proper.

In use, the user first applies a coloring material or ink to the indentor marking edge, most conveniently by simply rolling that edge on a conventional stamp inking pad. The instrument is then applied to the sample by contacting the marking edge with the surface of the sample, and manually pressing the frame toward the sample and into abutting contact with portions of the sample immediately adjacent to that contacted by the marking edge. The instrument is then removed from the sample, and the length of the indentation is measured, such length being clearly shown by the transfer to the sample of the ink or other coloring material on the marking edge. A calibrated scale for a particular composition of sample being measured is conveniently attached to the frame for making the linear measurement just referred to.

Accordingly, it is the principal object of the present invention to provide a novel instrument for measuring and indicating the hardness of a sample of material such as a plastic foam material. Additional objects and purposes of the invention are to provide, in such an instrument, a thin elongated indentor having a convex marking edge, the indentor being resiliently mounted in a manually grasped frame; to provide in such an instrument a plate for contacting the sample, the plate being provided with a slot for loosely receiving therein the indentor; to provide, in such an instrument, calibration means including a calibration bar serving as the upper seat of resilient means biasing the indentor into the sample, the calibration bar being selectively positionable relative to the frame; and for other and similar objects and purposes as will become clear from a reading of the following description of a preferred embodiment of the invention, taken in connection with the accompanying drawing.

BRIEF DESCRIPTION OF THE DRAWING

FIG. 1 is a side elevational view of an instrument embodying the preferred invention, with portions broken away for clarity of illustration, the indentor being in its lower rest or inoperative position.

FIG. 2 is an end view of the instrument, taken on the arrows II—II of FIG. 1.

FIG. 3 is a vertical sectional view taken on the arrows III—III of FIG. 2, showing the instrument applied to a sample, with the indentor forced upwardly as seen in the drawing against the force of the resilient means biasing it downwardly.

FIG. 4 is a plan view showing the application of the calibrated scale of the instrument to the measurement of the length of the indentation in the sample resulting from application of the instrument to the sample as shown in FIG. 3.

FIG. 5 is a fragmentary side elevational view illustratively showing the indentor marking edge penetrating into a sample whose hardness is appreciably less than the hardness of the sample shown in FIGS. 3 and 4.

DETAILED DESCRIPTION

Referring now in detail to the drawing, and first to FIGS. 1 and 2 thereof, a frame indicated generally at 10 may desirably be made up of a metal strap bent to provide a pair of parallel spaced sidewalls 12 and 14 joined at their upper portions by a horizontally disposed central yoke 16, the sidewalls terminating downwardly in out-turned flanges 17 and 18 respectively. Fixed to the lower surfaces of flanges 17 and 18 is a lower plate 20 which in the present illustrative embodiment of the invention has a planar lower surface 21. Plate 20 is fixed to flanges 17 and 18 by suitable means such as spot welding, and the plate lower surface 21, as will be later understood from the description of the manner of use of the present device, serves to contact the area of a sample immediately surrounding the exact portion of the sample whose hardness is being measured, and thereby serves to limit the movement of frame 10 toward the sample. For this reason, lower surface 21 of plate 21 is desirably contoured to be matingly congruent to the contour of the sample being tested by the present instrument. In the present illustrative form of the invention, it is assumed that the contour of the sample is planar or substantially so, and thus the contour of the lower surface 21 of the plate is also planar. If, on the other hand, the present instrument is used to measure the hardness of, say, a spherical sample, then the contour of the lower plate surface 21 should be matingly congruent therewith, i.e. should have a concave spherical contour with a radius of curvature substantially equal to that of the sample being tested.

Handle means may be provided for the present device, including in the present form of the invention a handle indicated generally at 24, here shown as comprising a piece of strap metal having a pair of spaced parallel sidewalls 25 and 26, each fastened to sidewalls 12 and 14 respectively of the frame by suitable fastening elements 27, the sidewalls 25 and 26 being integrally joined together by an upper enlarged cylindrical portion 28. As will be later understood, the handle 24, and particularly the upper cylindrical portion 28, serves to protect the calibrating means of the present device against damage in use, and also tends to minimize unauthorized tampering with the calibrating means.

An indentor indicated generally at 30 consists of a thin elongated blade of rigid material, preferably metal, having a downwardly directed convex marking edge 32 which is adapted to be forced downwardly as seen in the drawing into a sample whose hardness is being measured. Indentor 30 extends through a longitudinal slot 33 formed in plate 20, and is biased downwardly by resilient means to be described later. Means are provided for limiting such downward movement of the indentor relative to frame 10, and such means are here shown as including a pair of upwardly extending legs 34 and 36, fixed to indentor 30 and preferably formed integrally therewith. Legs 34 and 36 extend through respective slots 35 and 37 formed in yoke 16. The upper portions of legs 34 and 36 are provided with enlargements, here shown as transverse pins 38 and 39 respectively, each of which is downwardly abuttable against the yoke portion adjacent to the respective slots 35 and 37, thereby to limit downward movement of indentor 30.

Means are provided in accordance with the invention for biasing downwardly indentor 30, including calibration means for selectively adjusting the amount of force urging indentor 30 downwardly. In the present illustrative embodiment of the invention, the resilient means include a pair of compression springs 40 and 42 surrounding the lower portions of respective legs 34 and 36 and bearing at their lower ends downwardly against indentor 30 proper. The upper ends of springs 40, 42 bear against the lower surface of a horizontally disposed calibration bar indicated generally at 44, which has formed therein a pair of slots 45 and 46 through which the respective legs 34, 36 extend. Calibration bar 44 abuts upwardly against the lower ends of a pair of adjustment screws 47 and 48, which are threaded in yoke 16, and are provided with lock nuts 49 and 50 respectively.

It will thus be seen that, with handle 24 removed, the amount of compressive force in springs 40 and 42 urging indentor 30 downwardly can be adjusted by loosening lock nuts 49 and 50, and then turning the screws 47, 48, thereby raising or lowering the calibration bar 44 relative to frame 10 and relative to the rest position of indentor 30. After calibration, lock nuts 49 and 50 are tightened in conventional manner, and handle 24 is replaced in its operative position shown.

The manner of use of the present instrument will now be described, with reference to FIGS. 3, 4 and 5. As shown in FIG. 3, the user grasps handle 24, as by his thumb and fingers shown in dotted outline, and presses the instrument downwardly on a sample indicated generally at 60 until lower plate 20 contacts the upper surface of sample 60. This will cause the indentor marking edge 32, which the user has previously colored as by chalk, ink or similar material, to penetrate into sample 60 by a distance which, other factors being equal, is an inverse function of the hardness of the sample. It will also be seen that the length of the portion of the marking edge 32 which contacts the sample will also be an inverse function of the hardness of the sample.

The user then raises the instrument, thus removing the indentor from the sample and leaving a colored line on the sample having a length in the illustration shown in FIG. 3 indicated as a. As shown in FIG. 4, the user then measures the length of a, desirably using a calibrated scale plate indicated generally at 64, which for convenience may be fixed to the upper surface of one of the flanges, as flange 18, of the instrument frame. The scale indices on scale plate 64 may yield a reading of hardness or, as is preferred, may be calibrated to directly read density of the sample. It may be noted that, if the sample is of a resilient foam material, then the entire length a colored by the marking edge 32 will be clearly visible to the user. If the sample is not resilient, so that the indentation therein caused by indentor 30 remains even after the removal of the indentor, measurement of the length a may still be made without difficulty by measuring the distance between the spaced points, marked by coloring, where the indentor blade entered the sample.

In FIG. 5 there is fragmentarily shown, by way of illustration, the position of the indentor when the instrument is applied to measurement of the hardness of another sample, indicated generally at 70, having a hardness appreciably less than that of sample 60. As there shown, the length b of the marked line on the sample is appreciably longer than the length a, and measurement of length b by the scale of scale plate 64 will yield a lower reading of hardness, or of density of the sample.

There is thus provided a compact, simple and virtually full-proof instrument by which the user can quickly and conveniently measure the hardness or the density of a sample, such as of foam plastic. It will be readily understood that modifications and changes from the illustrative form of the invention hereinabove described and illustrated may occur to those skilled in the art, and all such modifications and changes not departing from the spirit of the invention are intended to be embraced within the scope of the appended claims.

I claim:

1. In an instrument for testing the hardness of a compressible sample and having a frame including means limiting downward movement of the frame relative to a sample and an indentor movably carried by the frame and resiliently biased downwardly relative thereto, the improvement wherein the indentor comprises a thin elongated blade provided with a convex downwardly directed marking edge for penetrating a sample and including a pair of spaced legs fixed to the blade near opposite ends thereof and projecting upwardly therefrom, and a resilient member associated with each leg for providing said resilient bias.

2. The invention as defined in claim 1, wherein the frame includes a horizontal member having a pair of openings formed therein for movably receiving the upper portions of the legs therethrough, and including an elongated calibration bar having a pair of openings registering with said frame member openings for movably receiving the upper portions of said legs therethrough, the legs having enlarged means adjacent their upper ends abuttable against the upper face of said frame member adjacent its said openings, the resilient members abutting upwardly against the bar, and means for selectively adjusting the vertical location of the bar relative to the frame member.

3. The invention as defined in claim 1 wherein the penetration of the edge into a sample is along a substantial portion of the length of the edge, and the side walls of said blade are parallel.

4. The invention as defined in claim 1 wherein said blade has parallel side walls.

5. The invention as defined in claim 1 wherein the penetration of the edge into a sample is along a substantial portion of the length of the edge.

6. The invention as defined in claim 1 wherein said edge carries thereon a coating of visually distinguishable marking material transferable to the penetrated portion of the sample.

* * * * *